United States Patent
Kemperman

(10) Patent No.: US 7,964,739 B2
(45) Date of Patent: Jun. 21, 2011

(54) PROCESS FOR THE PREPARATION OF ASENAPINE AND INTERMEDIATE PRODUCTS USED IN SAID PROCESS

(75) Inventor: Gerardus Johannes Kemperman, Oss (NL)

(73) Assignee: N.V. Organon, Oss (NL)

( * ) Notice: Subject to any disclaimer, the term of this patent is extended or adjusted under 35 U.S.C. 154(b) by 26 days.

(21) Appl. No.: 12/341,281

(22) Filed: Dec. 22, 2008

(65) Prior Publication Data

US 2009/0227803 A1     Sep. 10, 2009

Related U.S. Application Data

(60) Provisional application No. 61/019,012, filed on Jan. 4, 2008.

(30) Foreign Application Priority Data

Jan. 4, 2008   (EP) ..................................... 08150058

(51) Int. Cl.
*C07D 491/02*   (2006.01)

(52) U.S. Cl. .......................... 548/421; 548/416; 548/420
(58) Field of Classification Search .................. 548/416, 548/420, 421
See application file for complete search history.

(56) References Cited

U.S. PATENT DOCUMENTS 4,145,434 A * 3/1979 Van der Burg ................ 514/410

FOREIGN PATENT DOCUMENTS

| WO | WO 2006/106136 | 10/2006 |
| WO | WO 2007/046554 | 4/2007 |
| WO | WO 2008/003460 A1 * | 10/2008 |

OTHER PUBLICATIONS

Vader, J., et. al. ; "The Syntheses of Radiolabelled Org 5222 and its main metabolite Org 30526", Journal of Labelled Compounds and Radiopharmaceuticals, John Wiley, Chichester, GB, vol. 34, No. 9, 1994, pp. 845-869, XP008058294.
Padwa, A; Dent W.: "N-Benzyl-N-methoxymethyl-N-(trimethylsilyl) methylamine as an azomethine ylide equivalent: 2,6-dioxo-1-phenyl-4-benzyl-1,4-diazabicyclo[3.3.0]octane", Organic Syntheses, vol. 67, 1989, pp. 133-137, XP003478138.
Wildenberg, V.D., et. al.; "Biotransformation of Trans-5-Choloro-2-Methyl-2,3,3a,12b-Tetrahydro- . . . " Arzneimittel Forschung, Drug Research, ECV Editio Cantor Verlag, Aulendorf, DE, vol. 40, No. 5, 1990, pp. 540-544, XP008090109.
International Search Report for PCT/EP2008/068187; mailed Apr. 9, 2009; 4 pages.

* cited by examiner

*Primary Examiner* — Golam M Shameem
(74) *Attorney, Agent, or Firm* — Gerard Devlin; H. Eric Fischer

(57) ABSTRACT

The invention relates to a novel process for the preparation of asenapine, i.e. trans-5-chloro-2-methyl-2,3,3a,12b-tetrahydro-1H-dibenz[2,3:6,7]oxepino[4,5-c]pyrrole, as well as to novel intermediate products for use in said process.

7 Claims, No Drawings

PROCESS FOR THE PREPARATION OF ASENAPINE AND INTERMEDIATE PRODUCTS USED IN SAID PROCESS

CROSS-REFERENCE TO RELATED APPLICATION

This application claims the benefit of U.S. Provisional Application No. 61/019,012 entitled "PROCESS FOR THE PREPARATION OF ASENAPINE AND INTERMEDIATE PRODUCTS USED IN SAID PROCESS," filed Jan. 4, 2008, which is incorporated by reference in its entirety.

This present invention relates to a novel process for the preparation of trans-5-chloro-2-methyl-2,3,3a,12b-tetrahydro-1H-dibenz[2,3:6,7]oxepino[4,5-c]pyrrole, as well as to novel intermediate products for use in said process.

Trans-5-chloro-2-methyl-2,3,3a,12b-tetrahydro-1H-dibenz[2,3:6,7]oxepino[4,5-c]pyrrole, which is commonly known as asenapine, is a compound having CNS-depressant activity and having antihistamine and antiserotonin activities (U.S. Pat. No. 4,145,434 to van den Burg). The pharmacological profile of asenapine, its kinetics and metabolism, and the first safety and efficacy studies in human volunteers and in schizophrenic patients have been reviewed (De Boer et al., *Drugs of the Future*, 18(12), 1117-1123, 1993). It has been established that the maleate salt of asenapine, known as Org 5222, is a broad-spectrum, high potency serotonin, noradrenaline and dopamine antagonist.

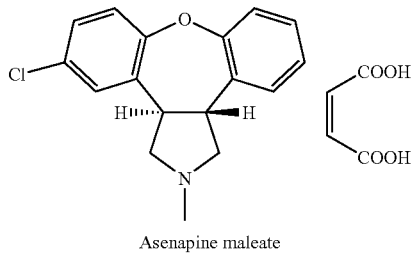

Asenapine maleate

Asenapine exhibits potential antipsychotic activity and may be useful in the treatment of depression (see international patent application WO 99/32108). A pharmaceutical preparation suitable for sublingual or buccal administration of asenapine maleate has been described in the international patent application WO 95/23600 (Akzo Nobel N.V.).

Asenapine maleate is now the subject of clinical studies, making large scale synthesis of the drug substance necessary.

A general methodology for the preparation of asenapine is disclosed in U.S. Pat. No. 4,145,434. Physical-chemical properties of the drug substance Org 5222 have been reported (Funke et al. *Arzneim.-Forsch/Drug. Res.* 40, 536-539, 1990). Additional synthetic methods for the preparation of Org 5222 and radiolabelled derivatives thereof have also been described (Vader et al., *J. Labelled Comp. Radiopharm.* 34, 845-869, 1994).

There is a need for synthetic procedures for the preparation of asenapine which can reliably be carried out on an industrial scale.

The present invention provides a process for the preparation of trans-5-chloro-2-methyl-2,3,3a,12b-tetrahydro-1H-dibenz[2,3:6,7]oxepino[4,5-c]pyrrole (asenapine) of Formula I,

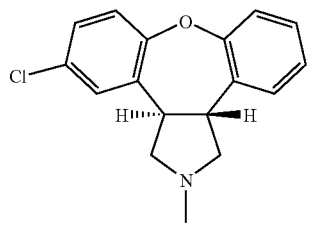

Formula I or a pharmaceutically acceptable salt thereof, characterised in that an E-stilbene derivative of Formula II,

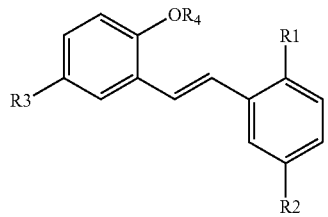

Formula II wherein $R_1$ is F, Br or I; $R_2$ and $R_3$ are different and are each selected from H and Cl; and $R_4$ is H or a hydroxyl protecting group;
is reacted with an azomethine ylide generated from a precursor tertiary amine of Formula A

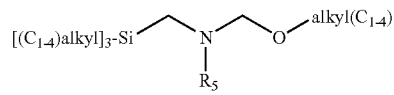

Formula A wherein $R_5$ represents an amino protecting group;
to provide a trans-pyrrolidine derivative of Formula III,

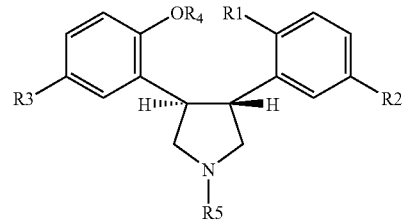

Formula III from which the hydroxyl protecting group $R_4$, when present, is removed, and which is subsequently treated under conditions which effect an intramolecular ring closure reaction to yield the oxepino compound of Formula IV, whereupon the amino

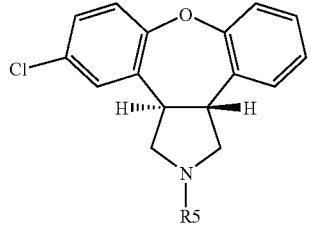

Formula IV protecting group $R_5$ is replaced by a methyl group, and the resulting asenapine of Formula I is optionally converted into a pharmaceutically acceptable salt thereof.

A preferred process of the invention is the process wherein $R_5$ represents an amino protecting group of formula —CHXY, wherein X is $(C_{1-6})$alkyl, vinyl (optionally substituted with halogen) or phenyl (optionally substituted with $(C_{1-3})$alkyl, $(C_{1-3})$alkoxy, $NO_2$, CN or halogen); and Y is H or phenyl; or X is $COOR_6$ and Y is H, $(C_{1-6})$alkyl, phenyl or benzyl;

$R_6$ is $(C_{1-4})$alkyl; and which amino protecting group is replaced by a methyl group either by reaction with 1-chloroethylchloroformate to give the compound of formula V, which is converted into the compound of Formula I by methylation, or by reaction with ethyl- or methylchloroformate to give the compound of formula VI,

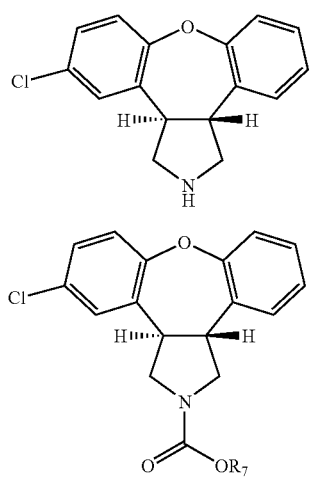

Formula V

Formula VI wherein $R_7$ is ethyl or methyl; which is converted into the compound of Formula I by reaction with a hydride reducing agent.

In the definition of Formula II, $R_4$ can be a hydroxy protecting group which is stable under the reaction conditions leading to the trans-pyrrolidine derivative of Formula III. Examples of such protecting groups are the tetrahydropyranyl group, a silyl protecting group or an acyl group. Further examples are known in the art. See, for example, Wuts, P. G. M. and Greene, T. W.: *Protective Groups in Organic Synthesis*, Third Edition, Wiley, New York, 1999. A preferred protecting group is the acyl group, the acyl group being derived from a $(C_{1-6})$alkyl carboxylic acid, such hexanoyl, pentanoyl, butanoyl, propionyl, acetyl and formyl. Especially preferred is the acetyl group.

The term $(C_{1-6})$alkyl as used in the definition of Formula I means a branched or unbranched alkyl group having 1-6 carbon atoms, like hexyl, pentyl, neopentyl, butyl, isobutyl, tertiary butyl, propyl, isopropyl, ethyl and methyl.

The term $(C_{1-4})$alkyl likewise means a branched or unbranched alkyl group having 1-4 carbon atoms, like butyl, isobutyl, tertiary butyl, propyl, isopropyl, ethyl and methyl.

The term $(C_{1-3})$alkyl means a branched or unbranched alkyl group having 1-3 carbon atoms, like propyl, isopropyl, ethyl and methyl.

In the term $(C_{1-3})$alkyloxy, $(C_{1-3})$alkyl has the meaning as defined above.

The term halogen means F, Cl, Br or I.

The term amino protecting group as used in the definitions of Formulae A, III, IV and VII means an amino protecting group that allows for the formation of an azomethine ylide shown in Formula VII, which is stable under the reaction conditions leading to the trans-pyrrolidine derivative of Formula III and under the reaction conditions leading to the oxepine compound of Formula IV.

Throughout this disclosure, compounds represented by structural formulae having a pair of bold and hashed wedged bonds, as shown, e.g., in the formula of compounds (I), (III), (IV), (V) and (VI) refer to the "trans" diastereoisomer. Each of the compounds may exist as a single enantiomer having the absolute stereochemical configuration indicated by the wedged bonds, or having the opposite absolute configuration, or as a mixture of enantiomers (e.g., racemate) having the relative stereochemical configuration indicated by the wedged bonds.

In a first reaction step of the process of the invention, an E-stilbene derivative of Formula II is reacted in a [3+2] dipolar cycloaddition reaction with an in situ generated azomethine ylide of Formula VII to provide a trans-pyrrolidine derivative of Formula III. It is thought that the reaction proceeds in a concerted manner in which all bonds are created simultaneously. Consequently, the stereochemistry is conserved in the product. When the reaction is started with an E-stilbene derivative, the trans pyrrolidine ring is formed exclusively. The stereoselectivity of the dipolar addition step in the process of the invention represents a large advantage with respect to the good overall yield of the process.

The required azomethine ylide, which is represented by the dipolar structure VII

Formula VII can be generated in situ from a precursor tertiary amine of Formula A

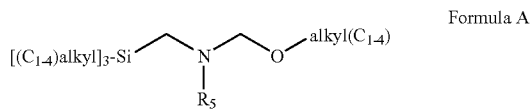

Formula A wherein $R_5$ represents an amino protecting group, via activation with trifluoroacetic acid or cesium fluoride (Hosomi, A. et al. *Chem. Lett.* 1117-1120, 1984) in an aprotic solvent such as dichloromethane, chloroform, toluene, tetrahydrofuran, ethers and esters such as ethylacetate and the like.

In a preferred embodiment of the invention $R_5$ represents an amino protecting group of formula —CHXY, wherein X is $(C_{1-6})$alkyl, vinyl (optionally substituted with halogen) or phenyl (optionally substituted with $(C_{1-3})$alkyl, $(C_{1-3})$alkoxy, $NO_2$, CN or halogen); and Y is H or phenyl; or X is $COOR_6$ and Y is H, $(C_{1-6})$alkyl, phenyl or benzyl; and $R_6$ is $(C_{1-4})$alkyl.

Especially preferred amino protecting groups $R_5$ are the benzyl, 2-methoxybenzyl, 4-methoxybenzyl, 2,4-dimethoxybenzyl, and the allyl group. These groups allow for easy and cheap preparations of the corresponding tertiary amines of formula A using commercially available starting materials.

The tertiary amines of formula A can be prepared from the alkylation of an appropriate amine $R_5$—$NH_2$, wherein $R_5$ has the meaning of —CHXY as previously defined, by [$(C_{1-4})$ alkyl]₃silylmethylchloride to yield a secondary amine which can be subsequently treated with formaldehyde in a (C₁₋₄) alcohol solution.

The preferred tertiary amines for use in the process of the invention are those according to formula

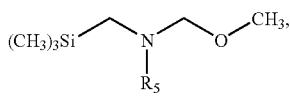

which are prepared by alkylation of the appropriate amine R₅—NH₂ by (chloromethyl)-trimethylsilane to yield a secondary amine which is subsequently treated with formaldehyde in methanol solution.

In a preferred embodiment, the dipolar addition reaction is carried out using stilbene derivatives of Formula II wherein R₄ represents a protecting group. The protecting group, such as an acetyl group, deactivates the hydroxy-phenyl group for electrophilic aromatic substitution reactions that may compete with the dipolar addition reaction leading to the pyrrolidine of formula II. As a result the occurrence of side products can be minimised.

In the second step of the process, a trans-pyrrolidine derivative of Formula IIIA,

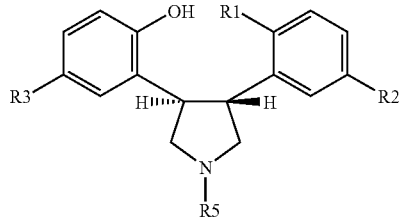

Formula IIIA is treated under conditions which effect an intramolecular ring closure reaction to produce trans-5-chloro-2-methyl-2,3,3a,12b-tetrahydro-1H-dibenz[2,3:6,7]oxepino[4,5-c]pyrrole (asenapine, Formula I).

The intramolecular ring closure reaction to form the 7-membered oxepine ring of asenapine can be performed with an Ullmann-type reaction, i.e. treatment of a compound of Formula IIIA in a solvent with copper(0) powder, with a copper(I) salt or with a copper(II) salt in the presence of a base at elevated temperatures (Ma, D., Cai, Q., *Organic Letters*, 5, 3799-3802, 2003; Buck, E., et. al, *Organic Letters* 4, 1623-1626, 2002; Sawyer, J. S., *Tetrahedron* 5045-5065, 2002). An additive, such as N,N-dimethylglycine, 2,2,4,4-tetramethyl-3,5-heptanedione (TMHD) or 8-hydroxyquinoline, may be used to increase the solubility of the copper ions. Suitable bases include Cs₂CO₃, K₂CO₃, pyridine, NaOH, KOH or CsF. Useful copper sources include Cu-powder, CuI, CuBr, CuCl, CuCO₃ (copper(II) carbonate), Cu(OAc)₂ (copper(II) acetate), Cu(OTf)₂ (copper(II) trifluoromethanesulfonate), Cu₂O or CuSO₄.

Suitable conditions for complete conversion of a compound of Formula IIIA to the oxepino derivative are the use of CuCl (0.25 eq.), N,N-dimethylglycine (0.25 eq.) and Cs₂CO₃ (1.1 eq.) in refluxing dioxane for about 24 hours. Solvents for use in the Ullman cyclisation reaction on an industrial scale at temperatures between about 80-110° C. are dimethylformamide (DMF), dimethylacetamide (DMA), N-methylpyrrolidone (NMP), pyridine, dioxane, toluene, xylene, diethyleneglycoldimethylether (Diglyme), 2-methyltetrahydrofuran, and the like.

Preferred reaction conditions for the Ullman cyclisation reaction at industrial scale are the use of dimethylacetamide or mixtures thereof with toluene as the solvent system, the use of Cs₂CO₃, NaOH, KOH or K₂CO₃ as the base, and the use of dimethylglycine in combination with copper(I)chloride as the catalyst.

A particularly useful embodiment of the invention is the process for the preparation of asenapine of Formula I,

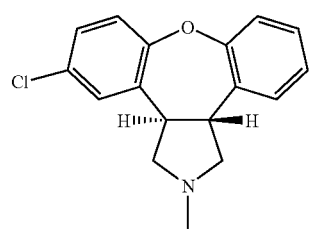

Formula I or a salt thereof, in which (E)-2-(2-bromostyryl)-4-chlorophenyl acetate,

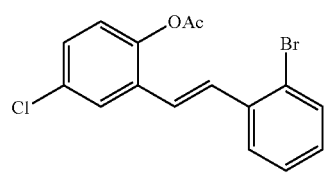

is reacted in an inert solvent, such as toluene, with the azomethine ylide generated in situ from N-methoxymethyl-N-trimethylsilylmethyl-N—R₅-amine, wherein R₅ represents an amino protecting group of Formula —CHXY, wherein X is (C₁₋₆)alkyl, vinyl (optionally substituted with halogen) or phenyl (optionally substituted with (C₁₋₃)alkyl, (C₁₋₃)alkoxy, NO₂, CN or halogen); and Y is H or phenyl; or X is COOR₆ and Y is H, (C₁₋₆)alkyl, phenyl or benzyl; and R₆ is (C₁₋₄)alkyl, with the aid of trifluoroacetic acid to provide trans-N—R₅-4-(2-bromophenyl)-3-(2-acetoxy-5-chlorophenyl)-pyrrolidine,

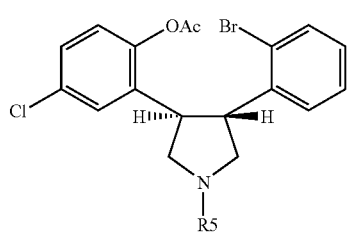

The pyrrolidine derivative is treated under basic conditions, such as aqueous alkali solution, to remove the acetyl group. Subsequent treatment of the deprotected pyrrolidine derivative under Ullmann conditions with the aid of a copper (I) salt to effect the intramolecular ring closure yields trans-5-chloro-2-R₅-2,3,3a,12b-tetrahydro-1H-dibenz[2,3:6,7]oxepino[4,5-c]pyrrole, in which R₅ has the meaning as given above.

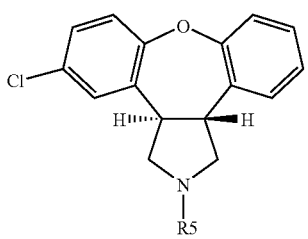

The protective group $R_5$ can be removed from this compound with 1-chloroethyl-chloroformate to yield trans-5-chloro-2,3,3a,12b-tetrahydro-1H-dibenz[2,3:6,7]oxepino[4,5-c]pyrrole, which can be transformed into asenapine (Formula I) by methylation, for example using reductive amination via treatment with formaldehyde in the presence of formic acid (Eschweiler-Clarke reaction).

Alternatively, the protective group $R_5$ can be removed by reaction with ethylchloroformate or methylchloroformate giving trans-5-chloro-2-ethoxy(or methoxy)carbonyl-2,3,3a,12b-tetra-hydro-1H-dibenz[2,3:6,7]oxepino[4,5-c]pyrrole. This compound can be converted into asenapine (Formula I) by treatment with a hydride reducing agent, preferably alane generated in situ from lithium aluminum hydride and aluminum chloride.

In one aspect therefore the invention provides the novel trans-oxepine derivatives of Formula VI, in which $R_7$ is an ethyl or a methyl group.

Formula VI

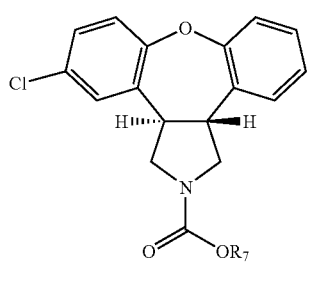

$R_7$ = methyl or ethyl

A further aspect of the present invention is the preparation of asenapine (Formula I) from a compound of Formula VI by reaction with a hydride reducing agent.

In yet another aspect the invention provides the novel trans-oxepine derivative of Formula IV, Formula IV

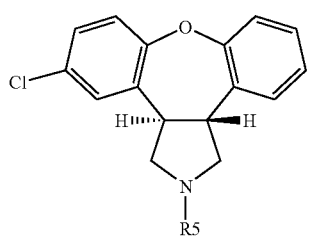

wherein $R_5$ represents an amino protecting group of formula —CHXY,
wherein X is $(C_{1-6})$alkyl, vinyl (optionally substituted with halogen) or phenyl (optionally substituted with $(C_{1-3})$alkyl, $(C_{1-3})$alkoxy, $NO_2$, CN, halogen);
and Y is H or phenyl; or X is $COOR_6$ and Y is H, $(C_{1-6})$alkyl, phenyl or benzyl; and
$R_6$ is $(C_{1-4})$alkyl; or a salt thereof.

A further aspect of the invention provides the novel trans-pyrrolidine derivative of Formula III, Formula III

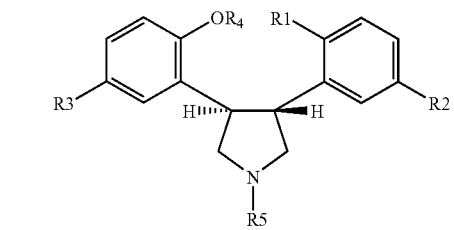

wherein $R_1$ is F, Br or I; $R_2$ and $R_3$ are different and are each selected from H and Cl; wherein $R_4$ is H or a hydroxyl protecting group, and wherein $R_5$ is an amine protecting group as previously defined, or a salt thereof.

The present invention further provides E-stilbene-derivative of Formula II

Formula II

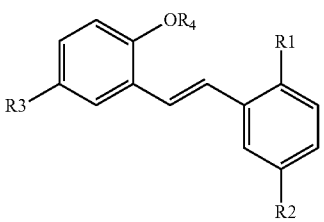

wherein $R_1$ is F, Br or I; $R_2$ and $R_3$ are different and are each selected from H and Cl; and wherein $R_4$ is H or a hydroxyl protecting group, as previously defined. These stilbene derivatives are useful intermediates in industrially producing the pharmaceutically active compound of Formula I, i.e. asenapine.

The E-stilbene derivatives of Formula II can for instance be prepared using a Wittig reaction in which a triphenylphosphonium halogenide of Formula IX, below, is reacted with an appropriate salicylic aldehyde of Formula X in refluxing solvents such as chloroform, tetrahydrofuran or mixtures thereof with ethanol, in the presence of an equivalent amount of a base, such as diisopropylethylamine, DBU, DABCO, potassium tert-butoxide or sodium ethoxide, wherein $R_1$, $R_2$ and $R_3$ are each as defined above for Formula II and III. The Wittig reaction typically results in a mixture of E- and Z-isomers, the best ratio's being approximately 70:30. The pure E-isomer (Formula II) may be isolated via chromatography.

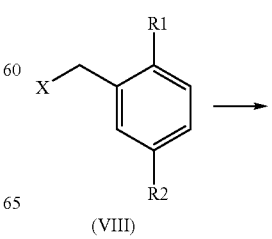

(VIII)

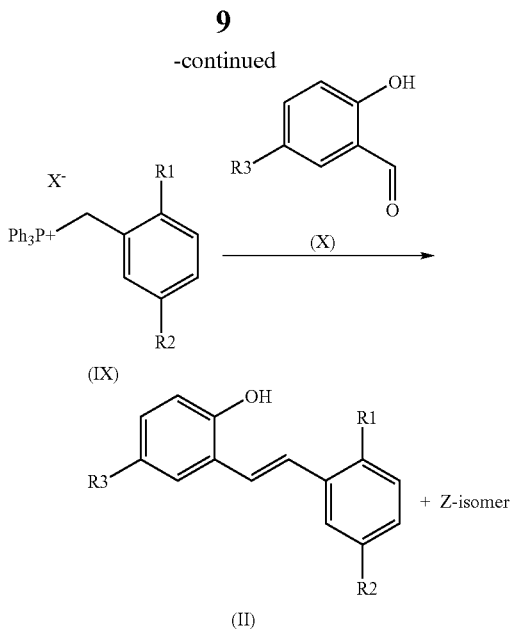

The triphenylphosphonium halogenide of Formula IX can be prepared by treatment of a compound of Formula VIII, wherein $R_1$ is F, Br or I, and $R_2$ is H or Cl, and wherein X represents halogen, preferably Cl of Br, with triphenylphosphine in refluxing toluene.

A preferred method of synthesizing E-stilbene derivatives of Formula II uses a phosphonate ester derivative having Formula XI, below. The phosphonate ester derivative can be prepared by heating a compound of Formula VIII, either neat or using a solvent such as toluene, with an equimolar amount of triethylphosphite (Davidsen, S. K.; Philips, G. W.; Martin, S. F. *Organic Syntheses*, Coll. Vol. 8, p. 451 (1993); Vol. 65, p. 119).

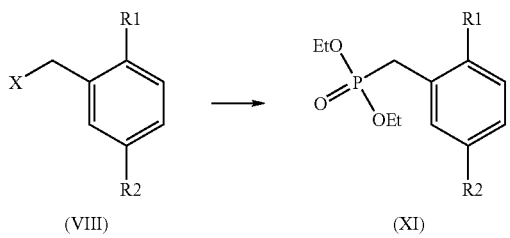

In a subsequent Wittig-Horner reaction (T. Kawasaki, et al., *J. Org. Chem.*, 66, 1200-1204, 2001; *Tet. Lett.* 43, 2449, 2001) the phosphonate ester of Formula XI is treated in a solvent, such as tetrahydrofuran, with a base, such as potassium tert-butoxide, butyllithium, sodiumhydride or sodiummethoxide, to produce an intermediate stabilized phosphonate anion which reacts with a salicylaldehyde derivative of Formula X to selectively yield an E-stilbene of Formula II.

Suitable acid addition salts of asenapine of Formula I and of the trans-pyrrolidine derivatives of Formula III can be obtained from the treatment with a mineral acid such as hydrochloric acid, hydrobromic acid, phosphoric acid and sulfuric acid, or with an organic acid such as, for example, ascorbic acid, citric acid, tartaric acid, lactic acid, maleic acid, malonic acid, fumaric acid, glycolic acid, succinic acid, propionic acid, acetic acid and methane sulfonic acid. The preferred acid addition salt of asenapine of Formula I is the maleate salt, i.e. Org 5222.

EXAMPLES

The following examples are illustrative and non-limiting and represent specific embodiments of the present invention. In each of the examples below, the compound asenapine (Formula I), and its precursor the trans-pyrrolidine derivative of Formula III, are racemates, and the pairs of bold wedged bonds or bold and hashed wedged bonds used in their structural formulae indicate relative stereochemical configuration.

General Methods:

NMR spectra were recorded on a Bruker DPX 400. Chemical shifts are reported in parts per million (ppm). $^1$H-NMR chemical shifts are referenced to TMS as internal standard (abbreviation s singlet; d doublet; t triplet, dd double doublet, m multiplet). Mass spectra were recorded on a PE SCIEX API 165. GC chromatograms were obtained using an Agilent HP6890N gas chromatograph outfitted with a Restek RTX-column. HPLC chromatograms were obtained using an Agilent HP1100 liquid chromatograph.

Example 1

(E)-2-(2-Bromostyryl)-4-chlorophenyl acetate

2-Bromobenzyl bromide (25 g, 0.100 mol) and toluene (25 ml) were heated to 100° C. Next triethyl phosphite (19.3 ml, 0.108 mol) was added over 30 minutes, while the temperature was kept below 116° C. The mixture was stirred for 4 hours at 115° C., while the toluene was distilled. The mixture was cooled to room temperature and diluted with tetrahydrofuran (THF; 16.5 ml). KOtBu (30.5 grams, 0.250 mol) was dissolved in THF (176 ml) and cooled to −10° C. The (2-bromobenzyl)-phosphonic acid diethyl ester solution was added at −5° C. Next chlorosalicylaldehyde (17.2 g, 0.110 mol) in THF (62 ml) was added at −10° C. The mixture was stirred for one hour at −5° C. to 0° C. When the reaction was complete acetic anhydride (24.5 ml, 0.36 mol) was added and the temperature was allowed to rise to 20° C. The reaction was stirred for another 15 min and then cooled to 5° C. The pH of the reaction mixture was adjusted to 5 by the addition of 200 ml 1N HCl. The organic layer was separated and washed with 200 ml saturated NaCl solution. The organic layer was evaporated under reduced pressure at 50° C., yielding (E)-2-(2-bromostyryl)-4-chlorophenyl acetate in 25.8 grams, (73%).

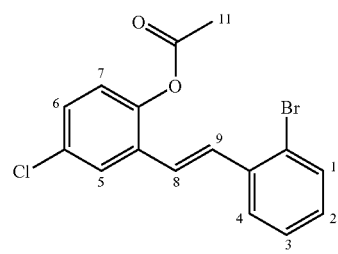

$^1$H-NMR (CDCl$_3$) δ (ppm): 2.38 (3H, s, H-11); 6.87 (1H, d, H-9), 7.19+7.34 (2×1H, 2×t, H-2+H-3), 7.26 (1H, d, H-6), 7.46 (1H, d, H-8), 7.60 (2H, dd, H-1+H-4), 7.68 (1H, d, H-5).

Example 2

2-Methoxy-N-(methoxymethyl)-N-[(trimethylsilyl)methyl]-benzenemethanamine

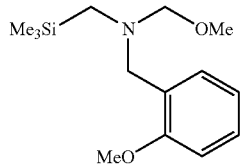

A: 2-Methoxy-N—[(trimethylsilyl)methyl]benzenemethanamine

A mixture of 2-methoxybenzylamine (25 g, 182.2 mmol) and trimethylsilylmethyl chloride (11.2 g, 91.1 mmol) in acetonitrile (140 ml) was refluxed overnight. Then the mixture was concentrated under vacuum at 70° C. with a rotary evaporator to remove all volatiles. The white residue was mixed with n-heptane (250 ml) and filtered over a glass filter. The salt residue was washed with n-heptane (2×25 ml). The combined heptane filtrates were concentrated under vacuum to give the crude product 2-methoxy-N-[(trimethylsilyl)methyl]benzenemethanamine as a clear oil (21.5 g; >100%) in quantitative yield. The product (92% pure according to GC-MS) was used without further purification.

$^1$H-NMR (CDCl$_3$) δ (ppm) 0.02 9H, s, (CH$_3$)$_3$Si; 2.00 2H, s, CH$_2$Si; 3.79 2H, s, CH$_2$; 3.83 3H, s, OCH$_3$; 6.89 2H, m, ArH; 7.23 2H, m, ArH.

B: 2-methoxy-N-(methoxymethyl)-N-[(trimethylsilyl)methyl]-benzenemethanamine The crude amine (21.5 g; theor. max. 91.1 mmol) was added slowly in portions over 30 minutes to a solution of 37% aqueous formaldehyde (9.4 g, 115.5 mmol, 1.2 eq.) and methanol (3.7 g, 115.5 mmol, 1.2 eq.) while stirring at 0° C. After 2 hours K$_2$CO$_3$ (12 g, 86.8 mmol) was added and the mixture was stirred for two additional hours. The organic layer was decanted. The sticky aqueous K$_2$CO$_3$ layer was washed with tBME (50 ml). The combined organic fractions were dried with Na$_2$SO$_4$, filtered and concentrated under vacuum to give the crude title compound as an oil (21.5 g, 80.4 mmol) in 88% c.y. over two steps. The product was used without further purification.

$^1$H-NMR (CDCl$_3$) δ (ppm) 0.03 9H, s, (CH$_3$)$_3$Si; 2.25 2H, s, CH$_2$Si; 3.25 3H, s, OCH$_3$; 3.80 5H, m, CH$_2$ and OCH$_3$; 4.03 2H, s, CH$_2$; 6.86 1H, d, J=8.4 Hz; 6.93 1H, dt, J=1.2 and 7.5 Hz; 7.22 1H, dt, J=1.8 and 7.8 Hz; 7.38 1H, dd, J=1.8 and 7.5 Hz.

Example 3

The method of Example 2 was further used to prepare the following compounds:

3A: 4-Methoxy-N-(methoxymethyl)-N-[(trimethylsilyl)methyl]-benzenemethanamine $^1$H-NMR (CDCl$_3$) δ: 0.03 9H, s, (CH$_3$)$_3$Si; 2.17 2H, s, CH$_2$Si; 3.23 3H, s, OCH$_3$; 3.69 2H, s, CH$_2$; 3.80 3H, s, OCH$_3$; 3.98 2H, s, CH$_2$; 6.83 2H, m, ArH; 7.24 2H, m, ArH.

3B: 2,4-Dimethoxy-N-(methoxymethyl)-N-[(trimethylsilyl)methyl]-benzenemethanamine $^1$H-NMR (CDCl$_3$) δ (ppm) 0.05 9H, s, (CH$_3$)$_3$Si; 2.22 2H, s, CH$_2$Si; 3.23 3H, s, OCH$_3$; 3.71 2H, s, CH$_2$; 3.77 3H, s, OCH$_3$; 3.80 3H, s, OCH$_3$; 3.99 2H, s, CH$_2$; 6.46 2H, m, ArH; 7.25 1H, d, J=8.1 Hz ArH.

Example 4

N-(methoxymethyl)-N-((trimethylsilyl)methyl)prop-2-en-1-amine

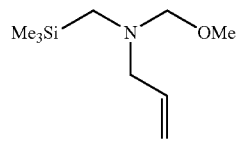

A: N-((trimethylsilyl)methyl)prop-2-en-1-amine

Allylamine (29.5 ml, 392.5 mmol) was warmed to 40° C. under nitrogen atmosphere. Chloromethyltrimethylsilane (25.0 ml, 180 mmol) was added very slowly to the allylamine while stirring. After the addition was complete the mixture was warmed to 70° C. for 24 hours. The mixture was cooled to 0° C. and water (25 ml) was added, followed by 2 N NaOH solution (75 ml). The mixture was stirred for one hour and was then extracted with tert-butyl methyl ether (tBME; 2×100 ml). The organic layer was dried with Na$_2$SO$_4$ and then concentrated under vacuum at 300 mbar at 70° C. to give pure N-((trimethylsilyl)methyl)prop-2-en-1-amine (21 g, 146.5 mmol) in 81% c.y.

$^1$H-NMR (CDCl$_3$) δ (ppm) 0.05 9H, s, (CH$_3$)$_3$Si; 2.06 2H, s, CH$_2$; 3.24 2H, d, J=6 Hz, CH$_2$; 5.12 2H, m; 5.88 1H, m. The product was used without further purification.

B: N-(methoxymethyl)-N-((trimethylsilyl)methyl)prop-2-en-1-amine

To N-((trimethylsilyl)methyl)prop-2-en-1-amine (21 g, 146.5 mmol) was slowly added aqueous formaldehyde (20 g; 37% w/w) while stirring at room temperature. After 5 minutes additional stirring methanol (8 g) was added followed by the addition of K$_2$CO$_3$ (24 g). The reaction mixture was stirred overnight at room temperature. Water (100 ml) was added, followed by addition of tert-butyl methyl ether (75 ml). The organic layer was separated. The aqueous layer was extracted with tert-butyl methyl ether (75 ml). The combined organic extracts were dried with Na$_2$SO$_4$. Concentration under vacuum gave N-(methoxymethyl)-N-((trimethylsilyl)methyl)prop-2-en-1-amine as a clear oil (24 g, 128.1 mmol) in 87% c.y.

$^1$H-NMR (CDCl$_3$) δ (ppm) 0.05 9H, s, (CH$_3$)$_3$Si; 2.16 2H, s, CH$_2$; 3.24 3H, s, OCH$_3$; 4.03 2H, s, CH$_2$; 5.12 2H, m; 5.81 1H, m. The product was used without further purification.

Example 5

N-(methoxymethyl)diphenyl-N-((trimethylsilyl)methyl)methanamine

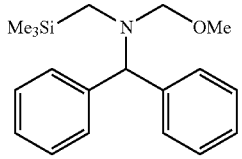

A: Diphenyl-N-((trimethylsilyl)methyl)methanamine

A mixture of benzhydrylamine (25 g, 136.4 mmol) and trimethylsilylmethyl chloride (8.39 g, 68.4 mmol) in acetonitrile (105 ml) was refluxed overnight. Then the mixture was concentrated under vacuum at 70° C. with a rotary evaporator to remove all volatiles. The white residue was mixed with n-heptane (150 ml) and filtered over a glass filter. The salt residue was washed with n-heptane (2×25 ml). The combined heptane filtrates were concentrated under vacuum to give the crude product as a clear, slightly yellow oil (23 g; >100%). Purification by chromatography on silica gel (700 ml) eluting with n-heptane (2000 ml), followed by n-heptane:ethyl acetate (10:1) gave pure diphenyl-N-((trimethylsilyl)methyl)methanamine (5.5 g, 20.4 mmol; 30%).
$^1$H-NMR (CDCl$_3$) δ (ppm) 0.05 9H, s, (CH$_3$)$_3$Si; 2.02 2H, s, CH$_2$Si; 4.71 1H, s, CH; 7.17-7.42 10H, m, ArH.

B: N-(methoxymethyl)diphenyl-N-((trimethylsilyl)methyl)methanamine

Diphenyl-N-((trimethylsilyl)methyl)methanamine (5.5 g, 20.4 mmol) was added dropwise to mixture of 37% aqueous formaldehyde (2.9 g) and methanol (1.5 g) while stirring at 0° C. After the addition was complete the reaction mixture was stirred for 2 hours at 0° C. K$_2$CO$_3$ (3 g) was added and the solidified mixture was warmed to room temperature. Methanol (4 ml) was added. After one hour stirring at room temperature, tBME (50 ml) and water (5 ml) was added. The organic layer was separated and dried with Na$_2$SO$_4$. Evaporation under vacuum gave the crude product N-(methoxymethyl)diphenyl-N-((trimethylsilyl)methyl)methanamine (7.05 g, max. 20.4 mmol) as an oil, which solidified on standing overnight at room temperature. The product was used without further purification.
$^1$H-NMR (CDCl$_3$) δ (ppm) 0.08 9H, s, (CH$_3$)$_3$Si; 2.23 2H, s, CH$_2$Si; 3.00 3H, s, OMe; 3.97 2H, s, CH$_2$O; 7.16-7.42 10H, m, ArH.

Example 6

N-(methoxymethyl)-N-((trimethylsilyl)methyl)butan-1-amine

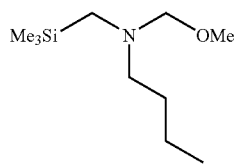

A: N-(trimethylsilyl)methyl-1-butanamine

A mixture of n-butylamine (25 g, 341.8 mmol) and trimethylsilylmethyl chloride (8.1 g, 66.0 mmol) was heated in a sealed tube at 200° C. for 16 hours. After cooling to room temperature the jelly mixture was mixed with 15% aqueous NaOH (50 ml). Extraction with n-heptane (100 ml) and drying of the organic layer with Na$_2$SO$_4$ gave after evaporation of the organic solvent at 75° C. at 450 mbar the crude N-(trimethylsilyl)methyl-1-butanamine (12.5 g; max. 66.0 mmol) as a clear oil. The product was used without further purification.
$^1$H-NMR (CDCl$_3$) δ (ppm) 0.03 9H, s, (CH$_3$)$_3$Si; 0.90 3H, t, CH$_3$; 1.25-1.51 5H, m, 2×CH$_2$ and NH; 2.06 2H, s, CH$_2$Si; 2.59 2H, t, NCH$_2$.

B: N-(methoxymethyl)-N-((trimethylsilyl)methyl)butan-1-amine

N-(trimethylsilyl)methyl-1-butanamine (12.5 g; max. 66.0 mmol) was added dropwise to a mixture of 37% aqueous formaldehyde (5.4 g) and methanol (2.2 g) while stirring at 0° C. After the addition was complete the reaction mixture was stirred for 90 minutes at 0° C. K$_2$CO$_3$ (6 g) was added and the mixture was stirred for an additional 2 hours. Then, tBME (100 ml) was added and the organic layer was separated. The aqueous layer was washed with tBME (50 ml). The combined organic layers were dried with Na$_2$SO$_4$. Evaporation at 75° C. under vacuum at 450 mbar gave the crude product N-(methoxymethyl)-N-((trimethylsilyl)methyl)butan-1-amine (13.5 g) as an oil in quantitative yield. The product was used without further purification.
$^1$H-NMR (CDCl$_3$) δ (ppm) 0.05 9H, s, (CH$_3$)$_3$Si; 0.90 3H, t, CH$_3$; 1.19-1.45 4H, m, 2×CH$_2$; 2.15 2H, s, CH$_2$Si; 2.58 2H, t, NCH$_2$; 3.24 3H, s, OMe; 4.02 2H, s, CH$_2$O.

Example 7

(R)-methyl 2-((methoxymethyl)((trimethylsilyl)methyl)amino)-2-phenylacetate

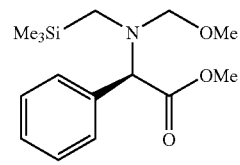

A: (R)-methyl 2-phenyl-2-((trimethylsilyl)methylamino)acetate

A mixture of (R)-phenylglycine methyl ester hydrochloride (2.1 g, 10.4 mmol), trimethylsilylmethyl chloride (1.29 g, 10.6 mmol), K$_2$CO$_3$ (2.7 g, 19.5 mmol) and KI (3.9 g, 23.5 mmol) in DMF (40 ml) was heated to 80° C. under nitrogen atmosphere for 18 hours. The mixture was concentrated under vacuum. Water (25 ml) and ethyl acetate (75 ml) was added. The organic layer was separated. The aqueous layer was extracted with ethyl acetate (50 ml). The combined organic layers were dried with Na$_2$SO$_4$ and concentrated under vacuum to give the crude product as a red oil. Purification by chromatography on silica gel (500 ml) eluting with ethyl acetate:n-heptane (1:3) gave (R)-methyl 2-phenyl-2-

((trimethylsilyl)methylamino)acetate (1.0 g, 3.98 mmol) as a yellow oil in 38% c.y. Mass: $M^{+1}$=252 found.

$^1$H-NMR (CDCl$_3$) δ (ppm) 0.04 9H, s, (CH$_3$)$_3$Si; 1.72 1H, br s, NH; 1.95 2H, dd, CH$_2$Si; 3.69 3H, s, OCH$_3$; 4.30 1H, s, CH; 7.27-7.36 5H, m, ArH.

B: (R)-methyl 2-((methoxymethyl)((trimethylsilyl)methyl)amino)-2-phenylacetate (R)-methyl 2-phenyl-2-((trimethylsilyl)methylamino)acetate (1.0 g, 3.98 mmol) was added to a mixture of 37% aqueous formaldehyde (784 mg) and methanol (310 mg) while stirring at 0° C. After two hours K$_2$CO$_3$ (1.0 g) was added and the mixture was stirred for an additional hour. Then, water (10 ml) was added and the mixture was extracted with ethyl acetate (2×50 ml). The combined organic layers were dried with Na$_2$SO$_4$. Concentration under vacuum gave the crude (R)-methyl 2-((methoxymethyl)((trimethylsilyl)methyl)amino)-2-phenylacetate as an oil (theor. max. 3.98 mmol). The product was directly used in the next step without further purification.

$^1$H-NMR (CDCl$_3$) δ (ppm) 0.03 9H, s, (CH$_3$)$_3$Si; 2.21 2H, dd, CH$_2$Si; 3.06 3H, s, OMe; 3.69 3H, s, OCH$_3$; 4.15 2H, m, OCH$_2$; 4.74 1H, s, CH; 7.26-7.42 5H, m, ArH.

Example 8

A: Racemic trans-2-(1-benzyl-4-(2-bromophenyl)pyrrolidin-3-yl)-4-chlorophenyl acetate

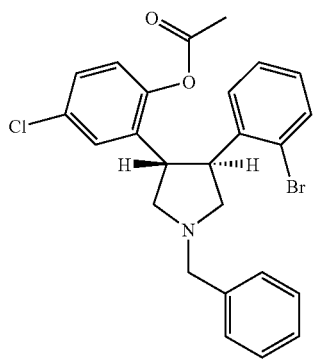

N-benzyl-N-methoxymethyl-N-(trimethylsilylmethyl)amine (5.0 g, 21.06 mmol) was added dropwise with a syringe over 30 minutes to a suspension of (E)-2-(2-bromostyryl)-4-chlorophenyl acetate (Example 1; 7.0 g, 19.9 mmol) in toluene (25 ml) containing trifluoroacetic acid (3 drops) while stirring at room temperature. After additional stirring for one hour water (10 ml) was added. The toluene layer was separated. The aqueous layer was extracted with toluene (25 ml). The combined organic layers were dried with Na$_2$SO$_4$ and evaporated under vacuum to give the crude cycloadduct as a clear and colorless oil, 10.76 g (>100%) in quantitative yield.

MS: $M^{+1}$=484, 486 found.

$^1$H-NMR (CDCl$_3$) δ (ppm) 2.36 3H, s; 2.64 1H, dd, J=6.9 and 9.0 Hz; 2.89 1H, dd, J=6.0 and 9.6 Hz; 3.08 1H, t, J=8.4 Hz; 3.29 1H, t, J=9.0 Hz; 3.55 1H, m; 3.66 1H, d, J=12.9 Hz; 3.76 1H, d, J=12.9 Hz; 3.87 1H, m; 6.88-7.67 12H, m, ArH.

B: Racemic trans-2-(1-benzyl-4-(2-bromophenyl)pyrrolidin-3-yl)-4-chlorophenol

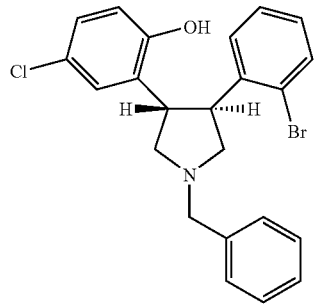

Ethanol (20 ml) was added to the crude cycloadduct (10.7 g) from above. The solution was concentrated under vacuum. Methanol (50 ml) was added to the residue followed by dilute aqueous KOH (2.5 g KOH in 12.5 ml water). A yellow solution was obtained. After 15 minutes stirring the pH was adjusted to pH ~8 with 2 N HCl. A sticky white gum precipitated after 5 minutes. Acetone (15 ml) was added and the resulting mixture was stirred overnight at room temperature. The mixture was extracted with toluene (2×50 ml), ethyl acetate (2×50 ml) and again toluene (50 ml). The combined organic layers were dried with Na$_2$SO$_4$ and concentrated under vacuum to give the crude title product as a clear oil, 9.3 g (21.0 mmol) in quantitative yield. According to $^1$H-NMR some small impurities were present. Purification by column chromatography on silica gel (600 ml), eluting with ethyl acetate:n-heptane=1:9 (R$_f$~0.2) gave the pure compound (3.0 g, 6.8 mmol) in 34% c.y. From concentrated less pure column fractions additional product (1.8 g, 4.1 mmol) was obtained in 20% c.y. by crystallization from acetone overnight. Overall yield is 54%. DSC analysis: m.p. 132.9° C.; 97.8% pure.

MS: $M^{+1}$=442, 444; $M^{-1}$=440, 442 found.

$^1$H-NMR (CDCl$_3$) δ (ppm) 2.34 1H, t, J=9.9 Hz; 2.99 1H, dd, J=8.1 and J=9.9 Hz; 3.31 2H, m; 3.59 1H, t, J=8.7 Hz; 3.70 1H, d, J=12.6 Hz; 3.95 1H, d, J=12.6 Hz; 4.02 1H, m; 6.75 1H, d, J=2.7 Hz; 6.85 1H, d, J=8.4 Hz; 7.07 2H, m; 7.26 7H, m; 7.52 1H, d, J=7.8 Hz; 12.34 1H, br s, OH.

Example 9

The methods of Example 8 were further applied to prepare the following compounds using the appropriate tertiary amines described in Examples 2, 3, 4, 5, 6 and 7:

9A: Racemic trans-2-(1-(2-methoxybenzyl)-4-(2-bromophenyl)pyrrolidin-3-yl)-4-chlorophenol

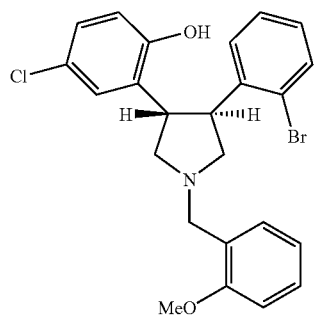

MS: M+1=472, 474; M−1=470, 472 found.

1H-NMR (CDCl3) δ (ppm) 2.37 1H, t, J=9.7 Hz; 2.98 1H, t, J=9.7 Hz; 3.25 2H, m; 3.59 1H, m; 3.80 1H, d, J=12.4 Hz; 3.87 3H, s, OMe; 3.91 1H, d, J=12.4 Hz; 4.00 1H, m; 6.71 1H, d, J=2.7 Hz; 6.81 1H, d, J=8.4 Hz; 6.93 2H, m; 7.07 2H, m; 7.31 4H, m; 7.50 1H, d, J=8.4 Hz.

9B: Racemic trans-2-(1-(4-methoxybenzyl)-4-(2-bromophenyl)pyrrolidin-3-yl)-4-chlorophenol

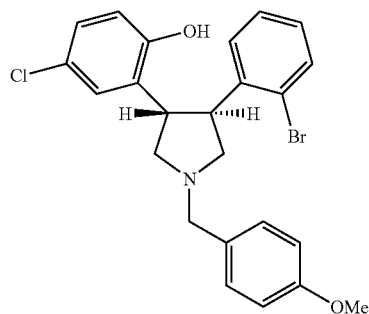

MS: M+1=472, 474; M−1=470, 472 found.

1H-NMR (CDCl3) δ (ppm) 2.34 1H, t, J=9.9 Hz; 2.98 1H, dd, J=7.8 Hz and J=9.9 Hz; 3.26 1H, d, J=9.9 Hz; 3.31 1H, dd, J=4.5 Hz and J=7.8 Hz; 3.63 1H, t, J=7.8 Hz; 3.66 1H, d, J=12.4 Hz; 3.82 3H, s, OMe; 3.90 1H, d, J=12.4 Hz; 4.03 1H, m; 6.78 1H, d, J=2.7 Hz; 6.87 2H, m; 7.09 2H, m; 7.31 5H, m; 7.53 1H, d, J=7.8 Hz.

9C: Racemic trans-2-(1-(2,4-dimethoxybenzyl)-4-(2-bromophenyl)pyrrolidin-3-yl)-4-chlorophenol

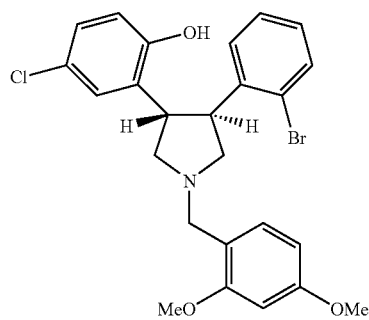

MS: M+1=502, 504; M−1=500, 502 found.

1H-NMR (CDCl3) δ (ppm) 2.34 1H, t, J=9.9 Hz; 2.94 1H, dd, J=7.8 Hz and J=9.9 Hz; 3.24 2H, m; 3.57 1H, t, J=7.8 Hz; 3.80-3.95 8H, m, 2×OMe and CH2; 1H, d, J=12.4 Hz; 3.82 3H, s, OMe; 3.90 1H, d, J=12.4 Hz; 4.02 1H, m; 6.43 2H, m; 6.73 1H, d, J=2.7 Hz; 6.80 1H, d, J=8.4 Hz; 7.00-7.10 2H, m; 7.16 1H, d, J=7.8 Hz; 7.32 2H, m; 7.50 1H, d, J=7.8 Hz.

9D: trans-2-(1-allyl-4-(2-bromophenyl)pyrrolidin-3-yl)-4-chlorophenol

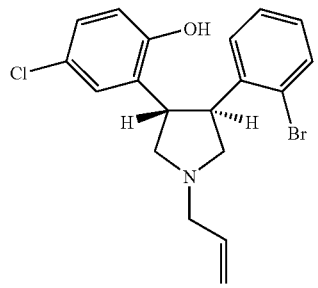

MS: M+1=392, 394; M−1=390, 392 found.

1H-NMR (CDCl3) δ (ppm) 2.33 1H, dd; 2.90 1H, dd; 3.30 4H, m; 3.71 1H, dd; 4.04 1H, m; 5.25 2H, m; 5.95 1H, m; 6.79 2H, m; 7.00-7.55 7H, m, ArH.

Example 10 trans-2-(1-benzhydryl-4-(2-bromophenyl)pyrrolidin-3-yl)-4-chlorophenol

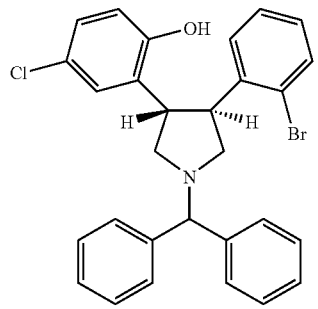

N-(methoxymethyl)diphenyl-N-((trimethylsilyl)methyl)methanamine (7.05 g, max. 20.4 mmol) was dissolved in dichloromethane (10 ml). The resulting solution was added over 5 minutes to a solution of (E)-2-(2-bromostyryl)-4-chlorophenyl acetate (7.0 g, 19.9 mmol) in toluene (25 ml), containing 3 drops of TFA at room temperature while stirring. After the addition was complete the mixture was stirred at room temperature for two hours to give a clear solution. Water (10 ml) was added followed by toluene (50 ml). The organic layer was separated and dried with Na2SO4. Concentration under vacuum gave the acetate (12.2 g; MS: M+1=560, 562 found). Methanol (50 ml) was added, followed by KOH (2 g) in water (12.5 ml). A yellow solution was obtained. After 15 minutes stirring 2N aq. HCl was added to pH ~8. Extraction with dichloromethane (2×100 ml), drying of the combined organic layers with Na2SO4 and concentration under vacuum gave the crude product as a sticky yellow oil (9.5 g). Purification by chromatography on silica gel (700 ml), eluting with ethyl acetate/n-heptane=1:9 (TLC; eluent: ethyl acetate/n-heptane: Rf=0.25; staining with iodine vapor) gave trans-2-(1-benzhydryl-4-(2-bromophenyl)pyrrolidin-3-yl)-4-chlorophenol (3.3 g, 6.36 mmol) in 32% c.y.

MS: M+1=518, 520; M−1=516, 518 found. 1H-NMR (CDCl3) δ (ppm) 2.38 1H, dd; 2.92 1H, dd; 3.16 1H, d; 3.31

1H, m; 3.67 1H, dd; 4.16 1H, m; 4.44 1H, d; 6.76 1H, d; 6.96 1H, d; 7.06-7.55 16H, m, ArH; 12.46 1H, br s.

Example 11 trans-2-(4-(2-bromophenyl)-1-butylpyrrolidin-3-yl))-4-chlorophenol

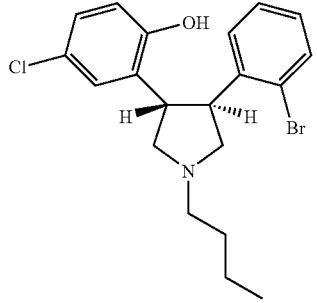

N-(methoxymethyl)-N-((trimethylsilyl)methyl)butan-1-amine (13.5 g, max. 66 mmol) was dissolved in toluene (50 ml). The resulting solution was added over 15 minutes to a solution of the (E)-2-(2-bromostyryl)-4-chlorophenyl acetate (23.1 g, 65.7 mmol) in toluene (80 ml), containing 5 drops of TFA at room temperature while stirring. After the addition was complete the mixture was stirred at room temperature for two hours to give a clear solution. Water (25 ml) was added and the organic layer was separated. The aqueous phase was extracted with toluene (50 ml). The combined organic layers were dried with $Na_2SO_4$. Concentration under vacuum gave the acetate (MS: $M^{+1}$=450, 452 found). Methanol (150 ml) was added, followed by KOH (6.6 g) in water (40 ml). A yellow solution was obtained. After 15 minutes stirring 2N aq. HCl was added to pH ~8. Extraction with dichloromethane (2×150 ml), drying of the combined organic layers with $Na_2SO_4$ and concentration under vacuum gave the crude trans-2-(4-(2-bromophenyl)-1-butylpyrrolidin-3-yl))-4-chlorophenol as a yellow oil (23 g, 56.3 mmol) in 86% c.y. The product was used without further purification. MS: $M^{+1}$=408, 410; $M^{-1}$=406, 408 found.

$^1$H-NMR (CDCl$_3$) δ (ppm) 0.94 3H, t, CH$_3$; 1.35-1.65 4H, m, 2×CH$_2$; 2.72 1H, t; 2.57-2.74 2H, m; 2.88 1H, dd; 3.29 2H, m; 3.74 1H, t; 4.04 1H, m; 6.76-7.69 7H, m, ArH.

Example 12

2-((3S,4S)-4-(2-bromophenyl)-1-((R)-1-phenylethyl)pyrrolidin-3-yl)-4-chlorophenol and 2-((3R,4R)-4-(2-bromophenyl)-1-((R)-1-phenylethyl)pyrrolidin-3-yl)-4-chlorophenol

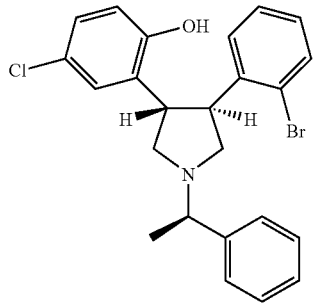

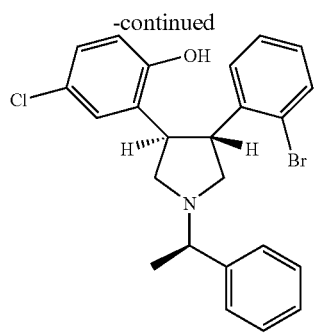

R(+)-N-methoxymethyl-N-(trimethylsilyl)methyl-1-phenylethylamine (5.0 g, 19.88 mmol, tech. 85%) was added dropwise to a solution of (E)-2-(2-bromostyryl)-4-chlorophenyl acetate (7.0 g, 19.9 mmol) in toluene (25 ml) containing 3 drops of TFA while stirring at room temperature. After 2 hours water (10 ml) was added and the mixture was extracted with toluene (2×50 ml). The combined organic layers were dried with $Na_2SO_4$ and then evaporated under vacuum to give the crude cycloadduct as an oil (11.2 g crude). Methanol (50 ml) was added, followed by a solution of KOH (2.5 g) in water (12.5 ml). After stirring for 30 minutes at room temperature the mixture was neutralized with 2N aq. HCl (ca. 10 ml). The mixture was extracted with toluene (2×75 ml) and the combined organic layers were dried with $Na_2SO_4$ and then evaporated under vacuum to give the crude product as a 1:1 mixture of the two title compounds which are diastereomers (9.8 g crude). Purification and partial separation of diastereomers by chromatography on silica gel (600 ml) eluting with ethyl acetate:n-heptane=2.5:97.5 (TLC: $R_f$=0.35-0.40 ethyl acetate:n-heptane=1:9) gave a 50 mg fraction containing one enriched diastereomer (72% d.e.; according to NMR), 3.0 g 47:53 mixture of diastereomers and a fraction enriched in the opposite diastereomer (74% d.e.). The absolute configuration of the first and second eluting isomers is not known.

MS: $M^{+1}$=456, 458; $M^{-1}$=454, 456 found.

$^1$H-NMR (CDCl$_3$) δ (ppm) first eluting isomer: 1.55 3H, d, CH$_3$; 2.24 1H, t; 2.96 1H, t; 3.32 2H, m; 3.53 2H, m; 3.93 1H, m; 6.79 1H, d, J=2.4 Hz; 6.87-7.37 10H, m, ArH; 7.47 1H, d, J=8.1 Hz.

$^1$H-NMR (CDCl$_3$) δ (ppm) second eluting isomer: 1.55 3H, d, CH$_3$; 2.40 1H, t; 2.78 1H, t; 2.92 1H, d; 3.20 1H, m; 3.55 1H, m; 3.93 1H, t; 4.13 1H, m; 6.71 1H, d, J=2.4 Hz; 6.78-7.36 10H, m, ArH; 7.53 1H, d, J=8.1 Hz.

Example 13

(R)-methyl 2-((3S,4S)-3-(2-bromophenyl)-4-(5-chloro-2-hydroxyphenyl)pyrrolidin-1-yl)-2-phenylacetate and (R)-methyl 2-((3R,4R)-3-(2-bromophenyl)-4-(5-chloro-2-hydroxyphenyl)pyrrolidin-1-yl)-2-phenylacetate

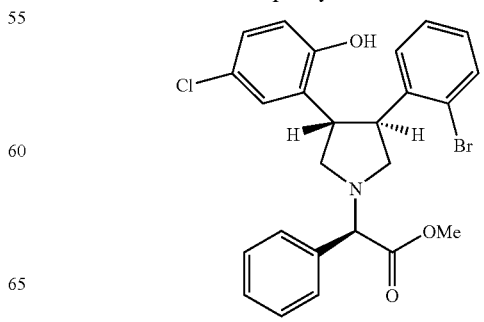

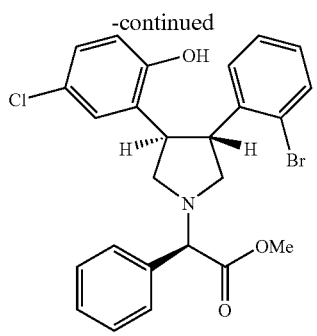

Crude (R)-methyl 2-((methoxymethyl)((trimethylsilyl)methyl)amino)-2-phenylacetate (theor. max. 3.98 mmol) was added at room temperature to a solution of (E)-2-(2-bromostyryl)-4-chlorophenyl acetate (1.32 g, 3.75 mmol) in toluene (5 ml), containing 3 drops TFA. The mixture was stirred overnight at room temperature. The reaction mixture was concentrated under vacuum to give the crude acetate as a slightly yellow solid. Methanol (25 ml) was added followed by a solution of KOH (1.0 g) in water (5 ml) while stirring at room temperature. After 15 minutes the yellow mixture was neutralized with 2N aq. HCl. The mixture was extracted with dichloromethane (3×75 ml). The combined organic layers were dried with $Na_2SO_4$. Concentration under vacuum gave the crude oily product as a mixture of the two title compounds which are diastereomers. According to LC-MS analysis 13% of the desired product was present. Purification by chromatography on silica gel (600 ml) eluting with ethyl acetate:n-heptane (1:9; $R_f$~0.2) gave a 580 mg fraction containing some impurities and a 150 mg fraction containing a 75:25 mixture of the title compounds shown below. Mass: $M^{+1}$=500, 502 found; $M^{-1}$=500, 498 found.

$^1$H-NMR (CDCl$_3$) δ (ppm) 2.30 0.75H, t; 2.59 0.25H, t; 2.89 1H, m; 3.07 0.75H, t; 3.23 0.25H, t; 3.36 1.25H, m; 3.51 0.75H, d; 3.70 2.25H, s, OCH$_3$; 3.74 0.75H, s, OCH$_3$; 3.85 0.25H, t; 4.02 0.75H, m; 4.15 0.25H, m; 4.18 0.75H, s; 4.22 0.25H, s; 6.79-7.69 12H, m, ArH.

Example 14 trans-5-chloro-2,3,3a,12b-tetrahydro-2-benzyl-1H-dibenz[2,3:6,7]-oxepino-[4,5-c]pyrrole

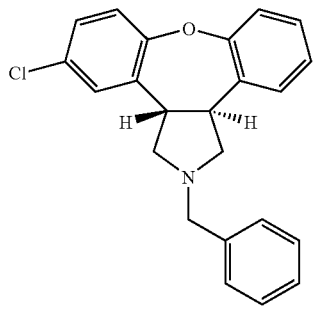

A mixture of racemic trans-2-(1-benzyl-4-(2-bromophenyl)pyrrolidin-3-yl)-4-chlorophenol (1.8 g, 4.07 mmol), cesium carbonate (2.65 g, 8.13 mmol, 2.0 eq.), N,N-dimethylglycine (165 mg, 1.6 mmol; 0.4 eq.) and CuI (310 mg, 1.6 mmol; 0.4 eq.) in dioxane (20 ml) was heated to reflux temperature while stirring under inert nitrogen atmosphere. After one hour the title product was formed according to mass analysis ($M^{+1}$=362, 364 found), but the conversion was not yet complete. Heating was continued overnight to give 98% conversion according to LC-MS. The reaction mixture was cooled to room temperature and was then filtered over a glass filter. The residual salts were washed with dioxane (25 ml). The combined filtrates were concentrated under vacuum to give the crude product as a brown oil. Toluene (150 ml) was added and the resulting solution was washed with concentrated aqueous ammonia (25 ml; 25%). The toluene layer was separated and dried with $Na_2SO_4$. Concentration under vacuum gave the title compound (1.47 g, 4.06 mmol) in quantitative yield as a brown oil, with ca. 78% purity according to LC-MS analysis. The product was used without further purification. MS: $M^{+1}$=362, 364 found.

$^1$H-NMR (CDCl$_3$) δ (ppm) 3.17 2H, m; 3.28 2H, m; 3.76 2H, m; 3.79 1H, d, J=13.2 Hz; 3.92 1H, d, J=13.2 Hz; 6.98-7.42 12H, m, ArH.

Example 15

The methods of Example 15 was further applied to prepare the following compounds using the appropriate pyrrolidin-derivatives described in Examples 8, 9, 10 and 11:

15A: trans-5-chloro-2,3,3a,12b-tetrahydro-2-(2-methoxybenzyl)-1 dibenz[2,3:6,7]-oxepino[4,5-c]pyrrole

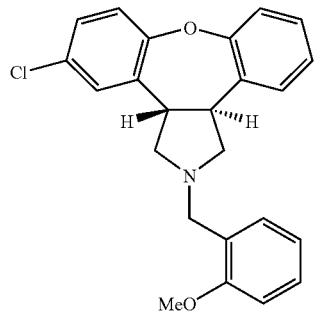

$^1$H-NMR (CDCl$_3$) δ (ppm) 3.21 2H, m; 3.36 2H, m; 3.65 2H, m; 3.87 3H, s, OMe; 3.91 2H, s; 6.90-7.46 11H, m, ArH.

15B: trans-5-chloro-2,3,3a12b-tetrahydro-2-(4-methoxybenzyl)-1H-dibenz[2,3:6,7]-oxepino[4,5-c]pyrrole

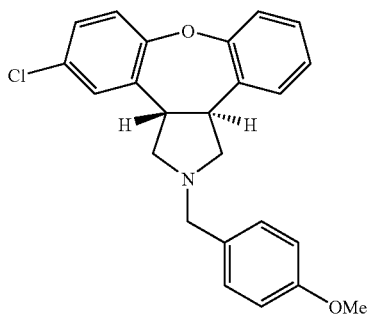

MS: $M^{+1}$=392, 394 found.

$^1$H-NMR (CDCl$_3$) δ (ppm) 3.14 2H, m; 3.26 2H, m; 3.63 2H, m; 3.72 1H, d, J=12.6 Hz; 3.83 3H, s, OMe; 3.85 1H, d, J=12.6 Hz; 6.89-7.34 11H, m, ArH.

15C: trans-5-chloro-2,3,3a,12b-tetrahydro-2-(2,4-dimethoxybenzyl)-1H-dibenz[2,3:6,7]-oxepino[4,5-c]pyrrole

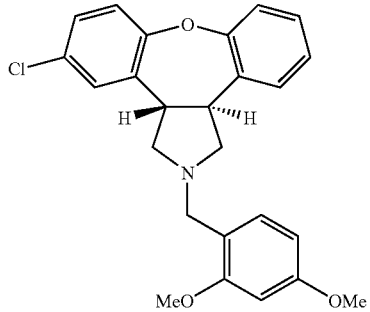

A mixture of racemic trans-2-(1-(2,4-dimethoxybenzyl)-4-(2-bromophenyl)pyrrolidin-3-yl)-4-chlorophenol (6.8 g, 13.54 mmol), cesium carbonate (8.83 g, 27.1 mmol, 2.0 eq.), N,N-dimethylglycine (558 mg, 5.42 mmol; 0.4 eq.) and CuI (1.03 g, 5.42 mmol; 0.4 eq.) in dioxane (75 ml) was heated to reflux temperature overnight while stirring under inert nitrogen atmosphere to give 90% conversion according to LC-MS ($M^{+1}$=422, 424 found). The reaction mixture was cooled to room temperature and was then filtered over a glass filter. The residual salts were washed with dioxane (25 ml). The combined filtrates were concentrated under vacuum to give the crude product as a brown oil. Toluene (150 ml) was added and the resulting solution was washed with concentrated aqueous ammonia (25 ml; 25%). The toluene layer was separated and dried with $Na_2SO_4$. Concentration under vacuum gave crude trans-5-chloro-2,3,3a,12b-tetrahydro-2-(2,4-dimethoxybenzyl)-1H-dibenz[2,3:6,7]oxepino[4,5-c]pyrrole (6.2 g) in quantitative yield as a brown oil, with ca. 70% purity according to LC-MS analysis. The product was used without further purification.

MS: $M^{+1}$=422, 424 found.

$^1$H-NMR (CDCl$_3$) δ (ppm) 3.18 2H, m; 3.32 2H, m; 3.63 2H, m; 3.80 2H, m; 3.83 3H, s, OMe; 3.85 3H, s, OMe; 6.52 1H, m; 7.02-7.33 9H, m, ArH.

15D: trans-5-chloro-2,3,3a,12b-tetrahydro-2-allyl-1H-dibenz[2,3:6.7]-oxepino[4,5-c]pyrrole

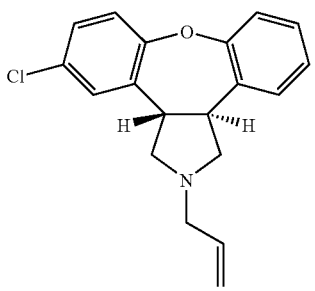

MS: $M^{+1}$=312, 314 found.

$^1$H-NMR (CDCl$_3$) δ (ppm) 3.13 2H, m; 3.31 4H, m; 3.63 2H, m; 5.22 2H, m; 5.97 1H, m; 7.03-7.26 7H, m, ArH. The product was used without further purification.

15E: trans-5-chloro-2,3,3a,12b-tetrahydro-2-benzhydryl-1H-dibenz[2, 3:6,7]-oxepino[4,5-c]pyrrole

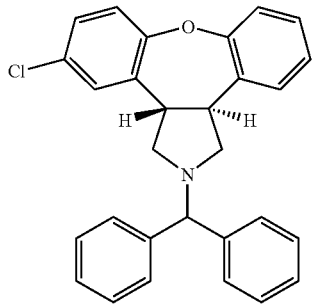

A mixture of trans-2-(1-benzhydryl-4-(2-bromophenyl)pyrrolidin-3-yl)-4-chlorophenol (1.0 g, 1.93 mmol), cesium carbonate (1.26 g, 3.85 mmol, 2.0 eq.), N,N-dimethylglycine (79.5 mg, 0.77 mmol, 0.4 eq.) and CuI (147 mg, 0.77 mmol, 0.4 eq.) in dioxane (10 ml) was heated to reflux overnight while stirring under inert nitrogen atmosphere. The reaction mixture was filtered over Celite on a glass filter. The residual solids were washed with dioxane (15 ml). The combined filtrates were concentrated under vacuum to give the title compound as an oil, 0.9 g in quantitative yield. The purity according to LC-MS was 72%. The product was used without further purification. MS: $M^{+1}$=437, 439 found. $^1$H-NMR (CDCl$_3$) δ (ppm) 3.01-3.20 4H, m; 3.65 2H, m; 4.61 1H, m; 6.93-7.55 17H, m, ArH.

15F: trans-5-chloro-2,3,3a,12b-tetrahydro-2-n-butyl-1 dibenz[2,3:6,7]-oxepino[4,5-c]pyrrole

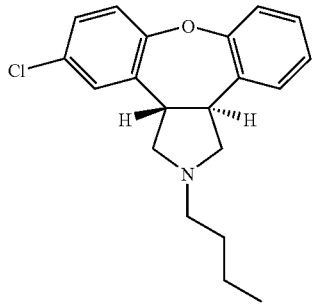

A mixture of crude trans-2-(1-butyl-4-(2-bromophenyl)pyrrolidin-3-yl)-4-chlorophenol (16.2 g, 39.63 mmol), cesium carbonate (25.8 g, 79.3 mmol, 2.0 eq.), N,N-dimethylglycine (1.63 g, 15.9 mmol, 0.4 eq.) and CuI (3.02 g, 15.9 mmol, 0.4 eq.) in dioxane (200 ml) was heated to reflux for 5 hours while stirring under inert nitrogen atmosphere. The reaction mixture was filtered over Celite on a glass filter. The residual solids were washed with dioxane (50 ml). The combined filtrates were concentrated under vacuum to give the title compound as an oil, 16.3 g in quantitative yield. The purity according to LC-MS was 79%. The product was used without further purification. MS: $M^{+1}$=328, 330 found.

$^1$H-NMR (CDCl$_3$) δ (ppm) 0.96 3H, t, CH$_3$; 1.25-1.62 4H, m, 2×CH$_2$; 2.58-2.76 2H, m; 3.12 2H, m; 3.26 2H, m; 3.61 2H, m; 7.02-7.26 7H, m, ArH.

Example 16 trans-5-chloro-2.3.3a,12b-tetrahydro-1H-dibenz[2,3:6,7]-oxepino[4,5-c]pyrrole (desmethylasenapine) from trans-5-chloro-2,3,3a,12b-tetrahydro-2-(4-methoxybenzyl)-1H-dibenz[2,3:6,7]-oxepino[4,5-c]pyrrole (Example 15B) Desmethylasenapine

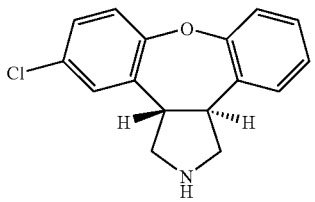

Alpha-chloroethyl chloroformate (15 ml) was added dropwise to a solution of trans-5-chloro-2,3,3a,12b-tetrahydro-2-(4-methoxybenzyl)-1H-dibenz[2,3:6,7]-oxepino[4,5-c]pyrrole (4.2 g, 10.7 mmol) in dichloromethane (100 ml) while stirring at room temperature. After 90 minutes the reaction mixture was concentrated under vacuum to give a foam. Methanol (50 ml) was added and the mixture was heated to reflux for one hour. Evaporation under vacuum gave the crude des-methylasenapine hydrochloride salt. Acetone (100 ml) was added and the mixture was stirred for 30 minutes. TBME (300 ml) was added and the mixture was stirred at room temperature for one hour. The precipitated salt was filtered over a glass filter and was dried under vacuum to give desmethylasenapine hydrochloride salt (1.9 g, 6.16 mmol) as a white solid in 58% c.y. with 98% purity according to LC-MS.

MS: $M^{+1}$=272, 274 found.

$^1$H-NMR (dmso-d6) δ (ppm) 3.43 2H, m; 3.66 2H, m; 3.90 2H, m; 7.14-7.36 7H, m; 9.69 1H, br s.

The same procedure was used for the preparation of des-methylasenapine hydrochloride salt from
trans-5-chloro-2,3,3a,12b-tetrahydro-2-benzyl-1H-dibenz [2,3:6,7]-oxepino[4,5-c]pyrrole (Example 14); from
trans-5-chloro-2,3,3a,12b-tetrahydro-2-(2-methoxybenzyl)-1H-dibenz[2,3:6,7]-oxepino[4,5-c]pyrrole (Example 15A); and from
trans-5-chloro-2,3,3a,12b-tetrahydro-2-(2,4-dimethoxybenzyl)-1H-dibenz[2,3:6,7]-oxepino[4,5-c]pyrrole (Example 15C).

Example 17 trans-5-chloro-2,3,3a,12b-tetrahydro-1H-dibenz[2,3:6,7]-oxepino[4,5-c]pyrrole (desmethylasenapine) from trans-5-chloro-2,3,3a12b-tetrahydro-2-allyl-1H-dibenz[2,3:6,7]-oxepino[4,5-c]pyrrole (Example 15D)

Tris(triphenylphosphine)rhodium(I)chloride (224 mg, 0.24 mmol, 1.9 mol %) was added to a stirred mixture of trans-5-chloro-2,3,3a,12b-tetrahydro-2-allyl-1H-dibenz[2,3:6,7]-oxepino[4,5-c]pyrrole (4.0 g, 12.83 mmol) in a mixture of acetonitrile (85 ml) and water (15 ml) at room temperature under inert nitrogen atmosphere. The mixture was then stirred at 90° C. for 3 hours until completion of reaction according to MS analysis ($M^{+1}$=272, 274 found; no starting material detected). Acetone (75 ml) was added to the residue and the solution was concentrated again under vacuum to give crude desmethylasenapine as an oil (5 g). Then 4 M HCl in dioxane (50 ml) was added to the crude product and the mixture was stirred at 75° C. for 30 minutes. Evaporation under vacuum of all volatiles gave des-methylasenapine as its HCl-salt. Tert-butyl methyl ether (100 ml) and acetone (10 ml) were added and the mixture was stirred at room temperature for 4 hours. The suspension was filtered over a glass filter and the residual salt was washed with a mixture of tBME (50 ml) and acetone (10 ml). Drying under vacuum gave 3.84 g (12.5 mmol) desmethylasenapine hydrochloride salt as a beige solid. $^1$H-NMR (dmso-d6) δ (ppm) identical as above.

Example 18 trans-5-chloro-2,3,3a,12b-tetrahydro-2-ethoxycarbonyl-1H-dibenz[2,3:6,7]-oxepino[4,5-c]pyrrole

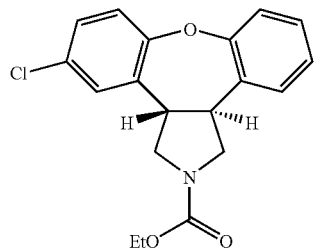

Ethyl chloroformate (5 ml) was added to a solution of trans-5-chloro-2,3,3a,12b-tetrahydro-2-benzyl-1H-dibenz[2,3:6,7]-oxepino[4,5-c]pyrrole (470 mg, 1.3 mmol) in toluene (30 ml). The reaction mixture was heated to reflux overnight under inert nitrogen atmosphere to give complete conversion. The resulting dark reaction mixture was concentrated under vacuum to give crude title compound as a black oil. MS: $M^{+1}$=344 found.

$^1$H-NMR (CDCl$_3$) δ (ppm) 1.33 3H, t, J=6.9 Hz, CH$_3$; 3.64 4H, m; 4.10 2H, m; 4.22 2H, q, J=6.9 Hz, CH$_2$; 7.08-7.28 7H, m, ArH.

Similarly trans-5-chloro-2,3,3a,12b-tetrahydro-2-ethoxycarbonyl-1H-dibenz[2,3:6,7]-oxepino[4,5-c]pyrrole was prepared from:
trans-5-chloro-2,3,3a,12b-tetrahydro-2-(2-methoxybenzyl)-1H-dibenz[2,3:6,7]-oxepino[4,5-c]pyrrole (Example 15A; quantitative yield); from
trans-5-chloro-2,3,3a,12b-tetrahydro-2-(4-methoxybenzyl)-1H-dibenz[2,3:6,7]-oxepino[4,5-c]pyrrole (Example 15B; quantitative yield); from
trans-5-chloro-2,3,3a,12b-tetrahydro-2-(2,4-dimethoxybenzyl)-1H-dibenz[2,3:6,7]-oxepino[4,5-c]pyrrole (Example 15C; quantitative yield); and from
trans-5-chloro-2,3,3a,12b-tetrahydro-2-allyl-1H-dibenz[2,3:6,7]-oxepino[4,5-c]pyrrole (Example 15D; quantitative yield).

Example 19 trans-5-chloro-2,3,3a,12b-tetrahydro-2-methyl-1H-dibenz[2,3:6,7]-oxepino[4,5-c]pyrrole (asenapine) from desmethylasenapine Method I (Eschweiler-Clarke Reductive Amination):
Desmethylasenapine hydrochloride salt (Example 16; 1.4 g, 4.55 mmol) was mixed with excess formic acid (6 g, 130 mmol) and water (12 ml). Aqueous formaldehyde (37%; 7 g, 233 mmol) was added and the solution was refluxed while stirring overnight. The resulting clear and colorless solution was concentrated under vacuum. Dichloromethane (100 ml) was added followed by the addition of 50% aq. NaOH. The basified aqueous layer was extracted twice with dichloromethane (2×50 ml). The combined organic layers were dried with $Na_2SO_4$. Concentration under vacuum gave pure trans-5-chloro-2,3,3a,12b-tetrahydro-2-methyl-1H-dibenz[2,3:6,7]-oxepino[4,5-c]pyrrole (asenapine) as a clear slightly yellow oil (1.1 g, 3.85 mmol) in 85% yield and 98% purity according to LC-MS. MS: $M^{+1}$=286, 288 found.

$^1$H-NMR (CDCl$_3$) δ (ppm) 2.56 3H, s, CH$_3$; 3.15 2H, m; 3.25 2H, m; 3.64 2H, m; 7.08 3H, m, ArH; 7.13 2H, m, ArH; 7.18 2H, m, ArH.

Method II (Reductive Amination):

Sodium triacetoxyborohydride (3.0 g, 14.0 mmol, 4.3 eq.) was added portionwise to a solution of desmethylasenapine hydrochloride salt (Example 16; 1.0 g, 3.25 mmol) and aqueous formaldehyde (1.3 ml, 5 eq.) in dichloromethane (20 ml) at room temperature. The reaction mixture was stirred for 90 minutes and was then concentrated under vacuum to dryness. Aqueous saturated NaHCO$_3$ solution (200 ml) and dichloromethane (300 ml) were added to the residue. The organic layer was separated and the aqueous layer was extracted with dichloromethane (25 ml). The combined organic layers were dried with Na$_2$SO$_4$. Evaporation under vacuum gave crude trans-5-chloro-2,3,3a,12b-tetrahydro-2-methyl-1H-dibenz[2,3:6,7]-oxepino[4,5-c]pyrrole (asenapine) with 81% purity, according to LC-MS.

MS: $M^{+1}$=286, 288 found. $^1$H-NMR data identical as above.

Example 20 trans-5-chloro-2,3,3a,12b-tetrahydro-2-methyl-1H-dibenz[2,3:6,7]-oxepino[4,5-c]pyrrole (asenapine) from trans-5-chloro-2,3,3a,12b-tetrahydro-2-ethoxycarbonyl-1H-dibenz[2,3:6,7]-oxepino[4,5-c]pyrrole Aluminium trichloride (4.1 g, 30.8 mmol, 2 eq.) was added to THF (20 ml) at 0° C. while stirring under inert nitrogen atmosphere and cooling with an ice bath. LiAlH$_4$ (3.6 g, 94.7 mmol, 6 eq.) was then added portionwise while stirring over 15 minutes. After the addition was complete the resulting grey mixture was stirred for 15 minutes at −10° C., while cooling with an ice-acetone bath. Additional THF (10 ml) was added. Then a solution of trans-5-chloro-2,3,3a,12b-tetrahydro-2-ethoxycarbonyl-1H-dibenz[2,3:6,7]-oxepino[4,5-c]pyrrole (Example 18; 5.4 g, 15.7 mmol) in THF (20 ml) was added dropwise over 15 minutes to the in situ prepared alane reagent while stirring and cooling at −10° C. After the addition was complete the reaction mixture was stirred for an additional hour at −10° C. and then for 30 minutes while warming to room temperature. The resulting reaction mixture was carefully poured out in portions to dilute aqueous NaOH (75 ml 30% NaOH and 175 ml water) in a 1000 ml Erlenmeyer flask. After 15 minutes stirring the mixture was extracted with toluene (3×150 ml). The combined organic layers were dried with Na$_2$SO$_4$. Evaporation under vacuum gave crude trans-5-chloro-2,3,3a,12b-tetrahydro-2-methyl-1H-dibenz[2,3:6,7]-oxepino[4,5-c]pyrrole (asenapine) (3.26 g, 11.44 mmol) in 73% c.y. as a brown oil. According to LC-MS ca. 60% pure. MS: $M^{+1}$=286, 288 found. $^1$H-NMR (CDCl$_3$) δ (ppm) identical data as above.

The invention claimed is:

1. A process for preparing asenapine of Formula I,

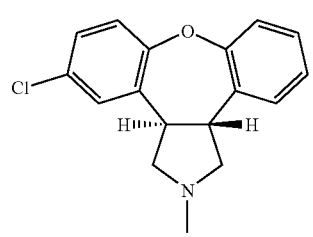

Formula I or a pharmaceutically acceptable salt thereof, wherein an E-stilbene derivative of Formula II,

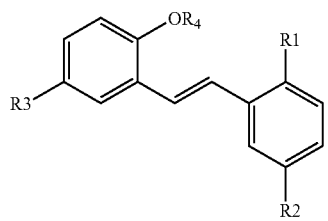

Formula II wherein
$R_1$ is F, Br or I;
$R_2$ and $R_3$ are different and are each selected from H and Cl; and
$R_4$ is H or a hydroxyl protecting group;
is reacted with an azomethine ylide generated from a precursor tertiary amine of Formula A

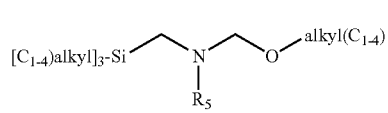

Formula A wherein $R_5$ represents an amino protecting group of formula —CHXY, wherein: X is $(C_{1-6})$alkyl, vinyl (optionally substituted with halogen) or phenyl (optionally substituted with $(C_{1-3})$alkyl, $(C_{1-3})$alkoxy, $NO_2$, CN or halogen); and Y is H or phenyl; or X is: $COOR_6$ wherein $R_6$ is $(C_{1-4})$alkyl; and Y is H, $(C_{1-6})$alkyl, phenyl or benzyl; to provide a trans-pyrrolidine derivative of Formula III,

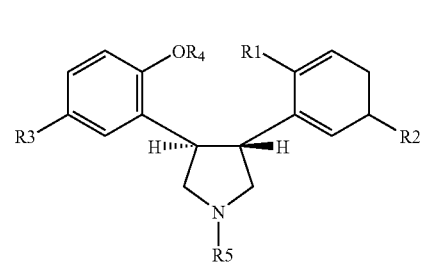

Formula III from which the hydroxyl protecting group $R_4$, when present, is removed, and which is subsequently treated under conditions which effect an intramolecular ring closure reaction to yield the oxepino compound of Formula IV,

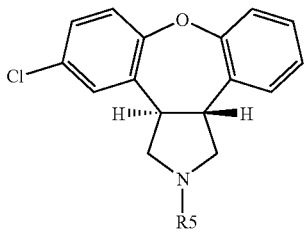

Formula IV whereupon the amino protecting group $R_5$ is replaced by a methyl group, and the resulting asenapine of Formula I is optionally converted into a pharmaceutically acceptable salt thereof.

2. The process of claim 1, wherein, after the compound of Formula IV has been formed, said $R_5$ amino protecting group is replaced by a methyl group either by reaction with 1-chloro-ethylchloroformate to give the compound of formula V, which is converted into the compound of Formula I by methylation, or by reaction with ethyl- or methyl-chloroformate to give the compound of formula VI,

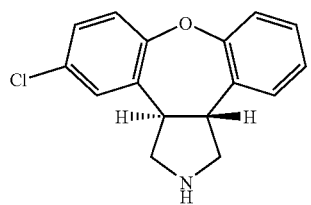

Formula V

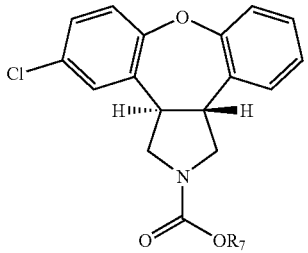

Formula VI wherein $R_7$ is ethyl or methyl; which is converted into the compound of Formula I by reaction with a hydride reducing agent.

3. The process of claim 1, wherein $R_1$ is Br or I.

4. The process of claim 3, wherein $R_1$ is Br, $R_2$ is H, and $R_3$ is Cl.

5. The process of claim 1, wherein the azomethine ylide is generated in situ from the precursor tertiary amine of formula

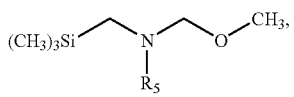

wherein:
$R_5$ represent —CHXY, wherein X is vinyl (optionally substituted with halogen) or phenyl (optionally substituted with $(C_{1-3})$alkyl, $(C_{1-3})$alkoxy, $NO_2$, CN or halogen); and Y is H.

6. The process of claim 1, wherein the azomethine ylide is generated with the aid of trifluoroacetic acid in an aprotic solvent.

7. A process for preparing the compound of Formula I,

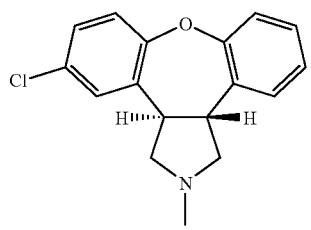

Formula I or a pharmaceutically acceptable salt thereof, wherein (E)-2-(2-bromostyryl)-4-chlorophenyl acetate,

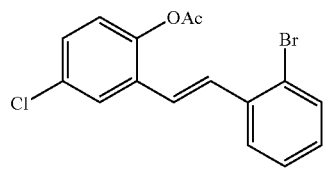

is reacted in an inert solvent with an azomethine ylide generated in situ from a precursor tertiary amine of Formula

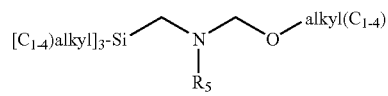

wherein:
$R_5$ represents an amino protecting group of Formula —CHXY, wherein: X is $(C_{1-6})$alkyl, vinyl (optionally substituted with halogen) or phenyl (optionally substituted with $(C_{1-3})$alkyl, $(C_{1-3})$alkoxy, $NO_2$, CN or halogen); and
Y is H or phenyl;
or:
$R_5$ represents an amino protecting group of Formula —CHXY, wherein: X is $COOR_6$ and $R_6$ is $(C_{1-4})$alkyl; and Y is H, $(C_{1-6})$alkyl, phenyl or benzyl;
with the aid of trifluoroacetic acid to provide the trans-N—$R_5$-2-bromophenyl-3-(2-acetoxy-5-chlorophenyl)-pyrrolidine derivative of Formula

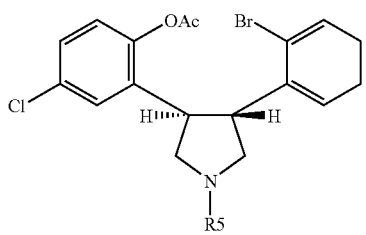

which pyrrolidine derivative is treated to remove the acetyl group, and which is subsequently treated under Ullmann conditions with the aid of a copper(I) salt to effect the intramolecular ring closure to give the trans-5-chloro-2—$R_5$I-2,3,3a,12b-tetra-hydro-1H-dibenz-[2,3:6,7]-oxepino-[4,5-c]pyrrole derivative

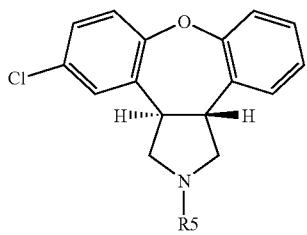

and subsequently the $R_5$-group is removed either by:
(i) using 1-chloroethylchloroformate to give trans-5-chloro-2-alkyl-2,3,3a,12b-tetrahydro-1H-dibenz[2,3:6,7]oxepino[4,5-c]pyrrole, which subsequently is converted into the compound of Formula I by N-methylation;
or
(ii) by reaction with methyl- or ethylchloroformate to give trans-5-chloro-2-methoxy(or ethoxy)carbonyl-2,3,3a,12b-tetra-hydro-1H-dibenz-[2,3:6,7]-oxepino-[4,5-c]pyrrole, which is subsequently converted into the compound of Formula I by reduction using a hydride reducing agent; and
optionally the compound of Formula I is converted to a pharmaceutically acceptable salt thereof.

* * * * *